United States Patent [19]

Haskell

[11] 4,404,413
[45] Sep. 13, 1983

[54] METHOD FOR THE PREVENTION OR INHIBITION OF POPCORN POLYMER IN ORGANIC MATERIAL CONTAINING VINYL COMPOUNDS

[75] Inventor: Weston W. Haskell, Houston, Tex.

[73] Assignee: Shell Oil Company, Houston, Tex.

[21] Appl. No.: 394,992

[22] Filed: Jun. 30, 1982

[51] Int. Cl.³ .............................................. C07C 7/20
[52] U.S. Cl. .......................................... 585/2; 585/950
[58] Field of Search ............... 585/2, 950; 570/103, 570/106

[56] References Cited

U.S. PATENT DOCUMENTS

| | | | |
|---|---|---|---|
| 1,950,438 | 3/1934 | Carothers | 570/106 |
| 2,136,334 | 11/1938 | Couman et al. | 570/106 |
| 2,188,772 | 1/1940 | Dreishack | 585/2 |
| 2,413,256 | 12/1946 | Suday | 585/2 |
| 2,483,778 | 10/1949 | Morrell et al. | 585/507 |
| 2,867,672 | 1/1959 | Hemmerich | 585/2 |
| 2,934,577 | 4/1960 | Graham | 585/2 |
| 3,565,855 | 2/1971 | Meltsner | 585/2 |

FOREIGN PATENT DOCUMENTS

| | | | |
|---|---|---|---|
| 635261 | 1/1962 | Canada | 585/2 |
| 2112705 | 10/1971 | Fed. Rep. of Germany | 585/2 |

OTHER PUBLICATIONS

Miller et al., J. Polymer Science, vol. IX, No. 5, 453–462, (1952).
Graham et al., Can. J. Research, B-26, 564–580, (1948).

*Primary Examiner*—Delbert E. Gantz
*Assistant Examiner*—Cynthia A. Prezlock
*Attorney, Agent, or Firm*—Ronald R. Reper

[57] ABSTRACT

The growth of butadiene "popcorn" polymer seeds in butadiene separation processes is inhibited by treatment of the butadiene with carbon disulfide or elemental phosphorus.

10 Claims, No Drawings

METHOD FOR THE PREVENTION OR INHIBITION OF POPCORN POLYMER IN ORGANIC MATERIAL CONTAINING VINYL COMPOUNDS

BACKGROUND OF THE INVENTION

This invention relates to a process for the prevention of popcorn polymer in organic materials by treating said material with at least one inhibitor selected from white phosphorus and carbon disulfide.

Popcorn polymer formation in organic materials containing vinyl compounds has long been known. Popcorn polymer is characterized by a white opaque voluminous structure always insoluble in the system where it is formed, as described, e.g., in Advances in Macromolecular Chemistry, Vol 1, Academic Press, N.Y. (1968), pp. 139–169 incorporated herein by reference.

Other names proposed in the literature for the instant popcorn polymers include sponge polymer, granular polymer, nodular polymer, cauliflower-like polymer, proliferous polymer, fluffy polymer and crusty polymer.

A characteristic of this polymer is its remarkable growing ability, i.e. it is able to consume and transform e.g. a vinyl compound into a popcorn phase without the need for an initiator and/or a cross-linking agent.

Growth of the polymer in industrial processing equipment can be disruptive of operations e.g., by plugging of tubular equipment such as heat exchangers and the like. Uncontrolled, the growing popcorn polymer has been known to exert tremendous force actually bulging heavy walled equipment, and bending and distorting trays and support beams within fractionation distillation equipment. Of great concern is that such polymer once active in industrial equipment is extremely difficult to deactivate and even trace quantities which remain on equipment after a clean-out, will remain active for long periods after being removed from the monomer, and act as seed to resume polymer growth when again in contact with the vinyl monomer. Manifestly such a problem is of deep concern in the operation of vinyl compound purification processes, particularly in processes designed for the separation of polymerization grade conjugated diolefins such as butadiene and isoprene from other organic materials such as mixtures of hydrocarbon resulting from cracking of petroleum and the like.

Over the years a number of materials have been suggested for inhibiting popcorn polymer growth including e.g. hydrogen sulfide (from hydrolysis of aqueous potassium sulfide) ethane-, propane- and hexane-thiol and to a lesser degree ethyl disulfide, however, these have not found wide application in the industrial processes.

SUMMARY OF THE INVENTION

The invention provides a process for the inhibition or prevention of popcorn polymer growth in organic materials comprising at least one vinyl compound which process comprises treating said organic material with a polymer inhibiting amount of an inhibitor selected from the group consisting of solid white phosporus, liquid phosphorus, phosphorus vapor carbon disulfide, and mixtures thereof.

DESCRIPTION OF PREFERRED EMBODIMENTS

The organic materials to be treated in accordance with the invention comprise at least about 50%w and preferably at least about 60%w of at least one vinyl compound, since it is known that it is possible to form popcorn polymers in systems containing up to 50% of an inert diluent or plasticizer.

The vinyl compound may comprise one or more mono-vinyl compounds such as styrene, acrylic acid and its esters such as methylacrylate, ethylacrylate, and butylacrylate; methacrylates such as methyl methacrylate, ketones such as methyl vinyl ketone, and nitriles such as acrylonitrile.

Exemplary divinyl compounds include e.g. butadiene, isoprene, dimethyl-2,3-buta-1,3-diene, chloroprene and bromoprene and mixtures of these.

Further suitable organic materials comprise mixtures of monovinyl and divinyl compounds such as styrene-butadiene, styrene-p-divinyl pyridine, 4-vinyl pyridine-butadiene and 2,5-dichloro-styrene-paradivinyl benzene.

The inhibitor treating agents according to the invention comprise white phosphorus, carbon disulfide and mixtures thereof.

Solid elemental phosphorus is known to exist in several allotropic forms. The white phosphorus (sometimes referred to as yellow phosphorus) suitably employed in the method of the invention may be colorless or white depending upon crystallite size or as is more usually found in commerce may have a slightly yellowish or straw color and will typically have a purity in excess of about 95%, preferably above 99% and most preferably above 99.9%. It may be employed as a solid or if applied at a temperature above about 44° C. will melt to a colorless or straw colored liquid. It has been found that red phosphorus is not an effective popcorn inhibitor. However it is when the phosphorus is melted, it is expected that the same liquid is obtained, even though the phosphorus may have been present in any of the white, red or black allotropes. Black phosphorus is rare and is formed from white phosphorus at high pressures above 10,000 $kg/cm^2$ and high temperatures of several hundred °C.

The other inhibitor used in the method of the invention is carbondisulfide. It is an extremely effective solvent for many organic compounds and for white phosphorus.

In accordance with the invention, popcorn polymerization is inhibited from formation in an organic material containing at least one vinyl compound by the presence of small amounts of at least one of phosphorus and carbon disulfide at a temperature from about 0°–280° C. preferably in the range from about 10° C. to about 250° C. Liquid phosphorus boils at 280.5° C. The amount of inhibitor required will vary depending upon the tendency of the particular monomer to form popcorn polymer, and also upon the amount of seed polymer, if any, present. Generally, amounts of inhibitor from about 0.0005 to about 3.0%w, and preferably from about 0.0010 to about 2.5%w, and most preferably from about 0.0050–1.0%w are sufficient. For systems in which phosphorus is insoluble in the organic material and the temperature is less than about 44° C. (the melting point of white phosphorus) the presence of solid white phosphorus in contact with the organic material may be sufficient to both deactivate any seed popcorn polymer and to inhibit any further polymer formation. At higher temperatures up to about 280° C. the organic material may be present in the vapor phase, the inhibitor will still be effective since the amount of phosphorus present in the vapor will be a function of the partial pressure of the phosphorus at the particular temperature. For example, butadiene at 58° C. has a vapor pressure of 5932 mm Hg at this temperature the partial pressure of phosphorus is 0.4 mm Hg resulting that phosphorus is present at 67 ppm in the gas phase. Pressure during treatment is not critical and may suitably be atmospheric, superatmospheric or subatmospheric.

Although carbon disulfide alone is less effective than phosphorus and requires somewhat larger amounts to stop popcorn polymer growth, it has been found that very low amounts of phosphorus may be added to the organic material by dissolving small amounts of phosphorus in carbon disulfide liquid and then adding the minimum amount required, as may be readily determined by one skilled in the art.

In order to more fully illustrate the nature of the present invention and the manner of practicing the same the following examples are presented.

EXAMPLE 1

Popcorn polymer seeds were grown in a butadiene atmosphere in sealed glass tubes placed in an oil bath at 58° C. The sealed glass tubes were mounted inside one-half inch diameter copper tubing. The glass tubes were 1 cm diameter and tapered to 4 mm tubing at the bottom. The 4 mm bottom end of the glass tube protruded from the bottom of the copper tube. The 4 mm bottom tubes was filled with sufficient butadiene so that the liquid/gas interface was visible below the copper tub. In this way the butadiene liquid level was visible while the tube was in the oil bath. After several days, the tubes were removed from temperature bath, cooled, and then broken open for weighing of the popcorn polymer.

When additives were included in the test these were added after the butadiene and before the pre-weighed popcorn polymer was placed in the glass tube. Elemental, white phosphorus was handled as follows: chips of phosphorus were cut from a bar of phosphorus in a nitrogen atmosphere. The chip was placed in a cup with several pieces of dry ice while in the nitrogen atmosphere. Then the cup was removed from the nitrogen atmosphere and the phosphorus chip was transferred to the tube.

For tests in which no inhibitor was present, after removal from the tube, the popcorn polymer seed retained its original dry, white, fluffy appearance. Occasionally after a test, a piece of popcorn polymer was extracted with n-heptane and then dried by pumping off the solvent in a vacuum. The popcorn was then weighed. Only on one occasion where the popcorn had a clearly visible coating of non-volatile liquid did the n-heptane extraction make any significant reduction in popcorn weight. To assure that the effects of the inhibitor were not influenced by a greater or lesser active polymer seed, only seed which experienced growth in the present tests were used in testing the inhibitors.

Initial tests were made with pure butadiene to establish a base growth constant which is described by the expression where $M = M_o e^{\alpha t}$ M = the mass of popcorn polymer including seed after t days $M_o$ = the initial mass of seed popcorn polymer e = base of natural logarithm, 2.71828 t = duration of test (days)

$\alpha$ = growth constant, day$^{-1}$

Pure butadiene resulted in growth constants around ten percent per day, 9.7%w averaged over the first seven samples shown in Table 1. Growth tests with pure butadiene could not be run more than seven to eight days because at these times the popcorn was beginning to wedge against the tube walls and broke up on removal. For this reason, data shown in Table 1 for a test at twelve days with no additive is suspect.

TABLE I
POPCORN POLYMER GROWTH TEST IN BUTADIENE IN SEALED GLASS TUBE, 58° C.

| Additive in Growth Atmosphere | Growth Constant[a] $\alpha$(day$^{-1}$) | Test Duration Days |
|---|---|---|
| none | 0.083[b] | 6 |
| none | 0.046[b] | 5 |
| none | 0.078[b] | 6 |
| none | 0.079[b] | 5 |
| none | 0.092[b] | 3 |
| none | 0.097[b] | 6 |
| none | 0.130 | 6 |
| none | 0.169 | 12 |
| phosphorus[c] | zero | 20 |
| phosphorus[c] | 0.004 | 30 |
| phosphorus[c] | 0.0045 | 28 |
| Carbon disulfide, 3% V | 0.006 | 19 |

[a] $m = m_o \exp(\alpha t)$ where t is time in days.
[b] Seeds from original source. Seeds used in remaining runs were from the same source, but had experienced growth in the present testing.
[c] Phosphorus is present as a second liquid phase. Equilibrium partial pressure of phosphorus is 0.4 mm Hg. Pressure of butadiene is 100 psig or 5932 mm Hg i.e., 67 ppm P.

Phosphorus prevented popcorn growth. In tests up to one month's duration weight gains of less than three milligrams out of 48 mg were observed (Table 1). Even this small weight gain may have been caused by diffusion of phosphorus into the popcorn polymer as the initially white popcorn was a bright yellow upon removal from the growth tube. This yellow popcorn visibly fumed in the air as it warmed up and usually gained a few tenth milligrams even as it was degassing butadiene. After exposure to air the yellow popcorn removed from the butadiene plus phosphorus growth tests resumed growth when placed in pure butadiene.

Were phosphorus was added to the butadiene growth tubes the phosphorus existed as a separate liquid phase. Thus, the equilibrium partial pressure of phosphorus present in the tube depends only on temperature. Partial pressure of phosphorus gas phase species over white phosphorus is 0.4 mm Hg. As butadiene pressure in the tube is 100 psig, phosphorus is present at 67 ppmv in the gas phase.

Carbon disulfide at 3%V in butadiene prevents popcorn growth. Again, as with phosphorus, the small weight gain with carbon disulfide may also result from diffusion of $CD_2$ into the polymer.

EXAMPLE 2

The procedure of Example 1 was repeated except that red phosphorus was used in place of the white phosphorus and the test duration was 7 days. The growth constant with red phosphorus present was 0.102 compared to 0.129 for butadiene with no additive in the growth atmosphere.

EXAMPLE 3

The procedure of Example 1 was repeated except that the butadiene was replaced with styrene. The styrene with no white phosphorus present was totally converted to solid popcorn polymer with 48–72 hours. By comparison with phosphorus present the styrene exhibited no popcorn polymer after 11 days; however, after 31 days the styrene had polymerized, which polymer by visual inspection appeared to be about 50% popcorn polymer and 50% thermal polymer.

EXAMPLE 4

The procedure of Example 1 was repeated except that the butadiene was replaced with vinyl acetate. After 24 days when testing of the uninhibited material was discontinued, the vinyl acetate without white phosphorus was extremely viscous at 58° C. and non-flowable at room temperature. This is in contrast to no apparent increase in viscosity at either temperature for the vinyl acetate with white phosphorus after 42 days duration at 58° C.

What is claimed is:

1. A method for the inhibition or prevention of popcorn polymer growth in organic materials comprising at least 50%w of at least one vinyl compound which method comprises treating said organic material with a polymer-inhibiting amount of an inhibitor selected from the group consisting of solid white phosphorus, liquid phosphorus, and phosphorus vapor.

2. A method as in claim 1 wherein the organic material comprises at least about 60%w of vinyl compound(s).

3. A method as in claim 1 wherein said at least one vinyl compound contain at least two double bonds.

4. A method as in claim 3 wherein said at least one vinyl compound comprises a conjugated diene.

5. A method as in claim 4 wherein said at least one vinyl compound is at least one of butadiene and isoprene.

6. A method as in claim 1 wherein said inhibitor is white phosphorus.

7. A method as in claim 1 wherein the amount of inhibitor is in the range from about 0.0005 to about 3%w of the organic material.

8. A method as in claim 1 wherein the temperature of treatment is in the range from about 0° to 280° C.

9. A method as in claim 1 wherein for said treating said phosphorus inhibitor is applied mixed with carbon disulfide.

10. A method for the inhibition or prevention of popcorn polymer growth in organic material comprising at least 50%w of at least one vinyl compound which method comprises treating said organic material with a polymer-inhibiting amount of carbon disulfide.

* * * * *